(12) United States Patent
Juhl et al.

(10) Patent No.: US 7,951,528 B2
(45) Date of Patent: May 31, 2011

(54) USE OF TRANSTHYRETIN AS A BIOMARKER FOR COLORECTAL ADENOMA AND/OR CARCINOMA; METHOD FOR DETECTION AND TEST SYSTEM

(75) Inventors: Hartmut Juhl, Hamburg (DE); Kerstin David, Hamburg (DE)

(73) Assignee: Invidumed GmbH, Hamburg (DE)

( * ) Notice: Subject to any disclaimer, the term of this patent is extended or adjusted under 35 U.S.C. 154(b) by 177 days.

(21) Appl. No.: 11/660,070

(22) PCT Filed: Aug. 13, 2004

(86) PCT No.: PCT/EP2004/009124
§ 371 (c)(1),
(2), (4) Date: Feb. 12, 2007

(87) PCT Pub. No.: WO2006/015616
PCT Pub. Date: Feb. 16, 2006

(65) Prior Publication Data
US 2007/0184499 A1    Aug. 9, 2007

(51) Int. Cl.
*C12Q 1/00*    (2006.01)
(52) U.S. Cl. .............................. 435/4; 435/7.1
(58) Field of Classification Search ................ 435/4, 7.1
See application file for complete search history.

(56) References Cited

U.S. PATENT DOCUMENTS
2001/0023066 A1    9/2001    Kinders et al.

FOREIGN PATENT DOCUMENTS
| | | |
|---|---|---|
| JP | 11-505019 | 5/1999 |
| JP | 2008-509407 | 3/2008 |
| WO | WO96/35955 | 11/1996 |
| WO | WO04/001072 | 12/2003 |
| WO | WO 2004/013609 | 2/2004 |
| WO | WO2006/015616 | 2/2006 |
| WO | WO2006/102526 | 9/2006 |

OTHER PUBLICATIONS

Kingsbury et al., May 2, 2008 The Journal of Biological Chemistry, 283, 11887-11896.*
Pasche, et al., Best Practice of Research Clinical Gastroenterology, vol. 16, No. 2, pp. 331-345(2002).
Basu, et al., J. Clin. Biochemistry and Nutrition, vol. 10, No. 1, pp. 65-70 (1991).
Gu, et al., Science in China, vol. 34, No. 11, pp. 1312-1318 (Nov. 1991).
Zhen, et al., Proceedings of the American Association for Cancer Research, vol. 45, p. 1303 (Mar. 2004).
Bullen, et al., Med. Ped. Oncol., vol. 3, pp. 289-300 (1977).
Milano, et al., J. Nat. Cancer Inst., vol. 61, No. 3, pp. 687-691 (Sep. 1978).
Hollinshead, et al., Nat. Cancer Inst. Monographs, vol. 49, pp. 187-192(Dec. 1978).
Fujimori, et al., Jap. Journal of Gastroenterological Surgery, vol. 24, No. 9, pp. 2363-2372 (1991).
Yuceyar, et al., Int. Surg., vol. 81, pp. 136-139 (1996).
Roboz, et al., www.aacrmeetingabstracts.org/cgi/content/abstract/2004/1/819 (2004).
Swahn, et al., Complement Activation in Ovarian Cancer, Poster Sessions, Abstract 1187, Oct. 24, 2001.
Official Action dated Oct. 26, 2009; in Japanese Patent Application No. 2007-525256.
Matsui, Rinshoi, vol. 25, No. 10, pp. 1922-1926(1999) and English Translation Thereof.
Decision of Refusal in corresponding Japanese Patent Application No. 2007-525176, dated Dec. 27, 2010 and English Translation Thereof.

* cited by examiner

*Primary Examiner* — Misook Yu
*Assistant Examiner* — Brad Duffy
(74) *Attorney, Agent, or Firm* — Elliot M. Olstein; Raymond J. Lillie (57) ABSTRACT

The invention is directed to a method for detecting colorectal adenoma and/or colorectal carcinoma comprising the steps: a) providing an isolated sample material which has been taken from an individual, b) determining the level of transthyretin in said isolated sample material, and c) comparing the determined level of transthyretin with a reference value. The invention is further directed to a method for discriminating between colorectal adenoma and colorectal carcinoma as well as to a method for monitoring the course of colorectal adenoma and/or colorectal carcinoma and/or the treatment of colorectal adenoma and/or colorectal carcinoma. Moreover, the invention is directed to a test system and an array for use in these methods. Furthermore, the invention is directed to the use of transthyretin as a biomarker for a detection of colorectal adenoma and/or colorectal carcinoma in an individual.

22 Claims, 6 Drawing Sheets

USE OF TRANSTHYRETIN AS A BIOMARKER FOR COLORECTAL ADENOMA AND/OR CARCINOMA; METHOD FOR DETECTION AND TEST SYSTEM

The present invention relates to the field of detection of colorectal adenoma and/or colorectal carcinoma.

Colorectal carcinoma is the third most frequently diagnosed carcinoma and the second leading cause of carcinoma death in Europe and in the United States. In 1996, an estimated 133 500 new cases of colorectal carcinoma were diagnosed and approximately 54 900 people died of this disease in the United States. The incidence of colorectal carcinoma is increasing, while the mortality rate of colorectal carcinoma is decreasing. Incidence of colorectal carcinoma increases with age, beginning at around 40 years of age, and it is higher for men than for women (60.4 for men versus 40.9 for women, per 100 000 per year).

In most patients, development of colorectal carcinoma follows a multistep progression from premalignant adenoma to invasive malignancies that have the propensity for metastasis. There is evidence that reduction in colorectal carcinoma morbidity and mortality can be achieved through detection and treatment of early-stage colorectal carcinomas and identification and removal of colorectal adenomatous polypes, which are the precursors of colorectal carcinoma.

Colorectal screening tests have been shown to achieve accurate detection of early stage colorectal carcinoma at its precursors, i. e. adenomatous polypes and/or flat neoplastic areas. Several tests are available as options for colorectal carcinoma screening. The screening tests encompass faecal occult blood testing (FOBT), flexible sigmoidoscopy, FOBT combined with flexible sigmoidoscopy and colonoscopy. The various screening tests differ from each other regarding performance, effectiveness, possible screening frequency, test complications, costs and acceptance of patient.

Screening by the faecal occult blood test is currently considered to be the optimal screening strategy in terms of cost-effectiveness. Occult blood in stool can be detected by chemical agents such as guaiac, through hemeporphyrin or immunological methods. The guaiac slide test Hemoccult (II) available from SmithKline Diagnostics is most widely used.

Various technical factors affect its clinical performance. Hemoccult has about 50% sensitivity for colorectal carcinomas and about 98% specificity, however, the sensitivity is low for polypes, at around 10% (Simon J B. (1998) Gastroenterologist 6:66-78. Review). Another important drawback of occult blood screening is the poor accuracy of prediction, only 10% of positive reactions prove to be due to colorectal carcinoma (Simon J B. (1998) Gastroenterologist 6:66-78. Review; Mandel J S et al. (1999) J. Natl. Cancer Inst. 91:434-437; Hardcastle J D et al. (1996) Lancet 348:1472-1477; Kronborg O et al. (1996) Lancet 348:1467-71; Winawer S J et al. (1997) Gastroenterology 112:594-642; Fletcher R H (1998) N. Engl. J. Med. 338:1153-1154).

Moreover, a faecal occult blood test does only provide results after progression of the disease to a certain stage. It would be desirable to have a test system allowing the detection of colorectal adenoma and/or colorectal carcinoma at an earlier point in time.

More recently developed immunological tests generally have high sensitivity, however, a poor specificity which remains an important problem. Other methods, such as genetic testings of stool samples for KRAS oncogenes and for p53 protein, are not yet cost-effective (Calistri D et al. (2003) Clin. Gastroenterol. Hepatol. 1:377-383; Schoen R E (2002) Nat. Rev. Cancer 2:65-70).

Endoscopy (Kavanagh A M (1998) Cancer Causes Control 9:455-462), using either the flexible sigmoidoscope or the colonoscope (Lieberman D A (1997) Gastroenterol. Clin. N. Am. 26: 71-83), is the most definitive means of detection, but has limitations.

The false negative rate for flat neoplastic lesions has been recognized and remains to be high (Kudo S (1997) Gastrointest. Endosc. Clin. N. Am. 7:87-98.). Colonoscopy permits examination of the colon with a low false negative rate for polypoid lesions of at least 10 mm in diameter. For this reason, the intervals allowed before re-examination are relatively long after a negative assessment (up to ten years) or up to five years after polypectomy.

However, patient compliance with such recommendation for reexamination after colonoscopy is poor. Moreover, a colonoscopy is costly and cumbersome. In view of the high costs of a generalized examination and the limited acceptance of a colonoscopy by the population this examination method has a limited application.

Isolated tissue samples, which are collected, can be tested for colorectal carcinoma and its precursors, colorectal adenoma, by various methods. DE 197 11 111A discloses a method using an in vitro determination of intraepithelial colon bacteria, components and reaction products thereof. Another method using HERG gene expression in tissue samples is disclosed in DE 102 24 534.

An object of the invention is to provide means allowing an early detection of colon adenoma and/or colon carcinoma.

It is a further object to provide a biomarker which can be used in the detection of colorectal adenoma and/or carcinoma.

Another object of the present invention is to provide a test system for detecting colorectal adenoma or carcinoma which is cost effective and can be widely used.

Moreover, the test system should be easy to handle and more convenient for the individual to be examined for colorectal adenoma and/or carcinoma.

The objects underlying the present invention are solved by the use of transthyretin as a biomarker for the detection of colorectal adenoma and/or colorectal carcinoma in an individual. The detection can be carried out in vivo and in vitro. Pursuant to a preferred embodiment, the detection is carried out in vitro.

The objects are further solved by a method for detecting colorectal adenoma and/or colorectal carcinoma comprising the steps:
 a) providing an isolated sample material which has been taken from an individual,
 b) determining the level of transthyretin in said isolated sample material,
 c) comparing the determined level of transthyretin with a reference value.

The objects are further solved by a method for discriminating between colorectal adenoma and colorectal carcinoma comprising the steps:
 a) providing an isolated sample material which has been taken from an individual,
 b) determining the level of transthyretin in said isolated sample material,
 c) comparing the determined level of transthyretin with a reference value.

The objects are also solved by a method for monitoring the course of colorectal adenoma and/or colorectal carcinoma and/or the treatment of colorectal adenoma and/or colorectal carcinoma comprising the steps:
 a) providing an isolated sample material which has been taken from an individual, b) determining the level of transthyretin in said isolated sample material,
c) comparing the determined level of transthyretin with a reference value.

The objects are solved as well by providing a test system for detecting colorectal adenoma and/or colorectal carcinoma in an individual comprising:
a) an antibody or a receptor which binds to an epitope of transthyretin,
b) a solid support which supports said antibody or receptor,
c) a reagent for detecting the binding of said epitope of transthyretin to said antibody or receptor.

The objects are furthermore solved by the provision of an array comprising detection molecules for detecting of colorectal adenoma and/or colorectal carcinoma in an individual comprising as detection molecule:
a) a nucleic acid probe immobilized to a solid support for binding to and detecting of mRNA encoding transthyretin, or
b) an antibody immobilized to a solid support for binding to and detecting of an epitope of transthyretin, or
c) a receptor immobilized to a solid support for binding to and detecting of an epitope of transthyretin,
wherein preferably each different amounts of detection molecules are immobilized to the solid support to increase the accuracy of the quantification.

Preferred embodiments are specified in dependent claims.

Pursuant to the present invention the term "biomarker" is meant to designate a protein or protein fragment which is indicative for the incidence of the colorectal adenoma and/or colorectal carcinoma. That means the "biomarker" is used as a detection agent or detection molecule.

The term "individual" or "individuals" is meant to designate a mammal. Preferably, the mammal is a human being such as a patient.

The term "healthy individual" or "healthy individuals" is meant to designate individual(s) not diseased of colorectal adenoma and/or colorectal carcinoma. That is to say, the term "healthy individual(s)" is used only in respect of the pathological condition of colorectal adenoma and/or colorectal carcinoma and does not exclude the individual to suffer from diseases other than colorectal adenoma and/or colorectal carcinoma.

The term "transthyretin" as used in the present invention also comprises truncated transthyretin, fragments of transthyretin, mutated transthyretin, or modified transthyretin. The modification of "transthyretin" can be due to enzymatic or chemical modification. Moreover, the term "transthyretin" is also used to designate monomeric or multimeric forms of transthyretin. For example, the term "transthyretin" especially covers the monomeric protein chain usually being part of the homotetrameric protein transthyretin.

The term "epitope" is meant to designate any structural element of transthyretin allowing the specific binding of an antibody, an antibody fragment, a protein or peptide structure or a receptor.

The process of isolating the sample material is not part of the invention. That is to say, the methods of the present invention are carried out with sample material such as a body fluid which already has been isolated. It is for example possible, to store the sample material to be tested in a freezer and to carry out the methods of the present invention at an appropriate point in time after thawing the respective sample material.

It has been surprisingly discovered by the present inventors that the protein transthyretin can be used as a biomarker for the detection of colorectal adenoma and/or carcinoma.

Transthyretin is also designated as prealbumin. Transthyretin is a tetrameric protein having a molecular weight of about 54 kDa that is synthesized mainly in the liver. Transthyretin is composed of four protein chains of about 14 kDa which can be identical. That is to say, transthyretin can be regarded as a homo tetrameric protein. It functions primarily as a binding protein for thyroxin, and as a carrier protein for retinal binding protein, which in turn is the transport protein for vitamin A (Schussler, G C Thyroid. (2000), 10:372; Hamilton, J A and Benson, M D Cell of Life Sci. (2001) 58:1491-1521).

Transthyretin is also reported to form complexes with amyloid β-protein. Aggregation of amyloid β-protein is associated with deposition of amyloid in the brain, which is a pathological feature of Alzheimer's disease.

Transthyretin has been further described as an indicator of the nutritional status, since serum levels of transthyretin decline with inadequate protein intake and during acute or chronic inflammation. In addition, transthyretin is suitable for monitoring the nutritional status because of its short half live of only 2-3 days (Pleban W E, Conn. Med. (1989) 53: 405-407; Bernstein L H and Ingenbleek Y, Clin. Chem. Lab. Med. (2002) 40:1344-1348).

WO 02/059621 discloses reagents which regulate transthyretin and reagents which bind to transthyretin gene products, thereby playing a role in preventing, ameliorating or correcting obesity and related dysfunctions.

It has been shown by SELDI (surface enhanced laser desorption/ionization) analysis that the monomeric transthyretin protein chain occurs in human plasma or serum at least in two variants having a molecular weight of 13,736 Da and 13,858 Da, respectively.

The different molecular weights are thought to be due to various post-translational modifications such as truncation, cysteinylation, and/or glutationylation. Cysteinylated transthyretin has a molecular weight of 13,871±11 Da, and the glutationylated transthyretin has a molecular weight of about 14.069±5 Da.

WO 03/001182 discloses the detection and isolation of homocysteinylated transthyretin from a biological fluid and its use as a marker for diagnosis of homocysteinemia, hyperhomocysteinemia and diseases associated therewith.

In some studies, transthyretin has been discussed as diagnostic marker for carcinoma. Suresh et al. (J. Clin. Pathol. (1991) 44: 573-575) described transthyretin as a useful marker in bronchopulmonary carcinoid tumors since 75% of the carcinoid tumors were positive for transthyretin. In another study, transthyretin was discussed as prognostic marker in epithelial ovarian carcinoma (Mahick et al., Gynecol. Obstet. Invest. (1994) 37: 135-140).

The inventors have now surprisingly found that the level of transthyretin in a body fluid is correlated with the incidence of colorectal adenoma and/or carcinoma in an individual.

Pursuant to the present invention, transthyretin can be measured in body fluids such as blood, blood plasma, blood serum, bone marrow, stool, synovial fluid, lymphatic fluid, cerebrospinal fluid, sputum, urine, mother milk, sperm, exudate and mixtures thereof.

Preferably, the body fluid has been isolated before carrying out the methods of the present invention. The methods of the invention are preferably carried out in vitro by a technician in a laboratory.

According to a preferred embodiment of the invention, transthyretin is measured in blood plasma or blood serum. Blood serum can be easily obtained by taking blood from an individual to be medically examined and separating the supernatant from the clotted blood.

The level of transthyretin in the body fluid, preferably blood serum, decreases with progressive formation of colorectal adenoma. The colorectal adenoma is a benign neoplasma which may become malign. When developing colorectal cancer from benign colorectal adenom, the level of transthyretin in body fluids, preferably blood serum, further decreases.

After transformation of colorectal adenoma into colorectal cancer, the pathological condition of the afflicted individual can be further exacerbated by formation of metastasis.

The present invention provides an early stage biomarker which allows to detect the neoplastic disease at an early and still benign stage. The early detection enables the physician to timely remove the colorectal adenoma and to dramatically increase the chance of the individual to survive.

Moreover, the present invention allows to monitor the level of transthyretin in a body fluid such as blood serum over an extended period of time, such as years.

The long term monitoring allows to differentiate between colorectal adenoma and colorectal carcinoma. The level of transthyretin can be routinely checked, for example, once or twice a year. If a decrease of the level of transthyretin is detected this can be indicative for colorectal adenoma. A further decrease of the level of transthyretin can then be indicative for the transformation into malign colorectal carcinoma.

Moreover, the course of the disease and/or the treatment can be monitored. If the level of transthyretin further decreases, for example after removal of the colorectal adenoma, this can be indicative for exacerbation of the pathological condition.

That means, the level of transthyretin is a valuable clinical parameter for detecting and/or monitoring of colorectal adenoma and/or colorectal carcinoma. The level of transthyretin in body fluids decreases very early after incidence of colorectal adenoma. Therefore, transthyretin or the level of transthyretin is an important clinical parameter to allow an early diagnosis and, consequently, an early treatment of the disease.

The method of the invention for detection of colorectal adenoma and/or colorectal carcinoma comprises the step of providing an isolated sample material which has been taken from an individual, then determining the level of transthyretin in the isolated sample material, and finally comparing the determined level of transthyretin with a reference value.

The reference value can be calculated as the average level of transthyretin determined in a plurality of isolated samples of healthy individuals. This reference value can be established as a range to be considered as normal meaning that the person is healthy. A fall below this range can then be indicative for the pathological condition of colorectal adenoma and/or colorectal carcinoma. This range of reference value can be established by taking a statistically relevant number of body fluid samples, such as serum samples, of healthy individuals as it is done for any other medical parameter range such as, e.g., blood sugar.

In an another embodiment of the present invention, the reference value can be an individual reference value calculated as the average level of transthyretin determined in a plurality of isolated samples taken from the individual over a period of time.

When monitoring the transthyretin level over an extended period of time, such as months or years, it is possible to establish an individual average level. The transthyretin level can be measured, for example, from the same blood serum sample when measuring blood sugar and can be used to establish an individual calibration curve allowing to specifically detect any individual decrease of the level of transthyretin.

In another aspect the present invention further provides a test system for detecting colorectal adenoma and/or colorectal carcinoma in an individual. The test system is based either on the specificity of an antibody or a receptor to bind to an epitope or a suitable structural element of transthyretin or a fragment of transthyretin. A receptor can be any structure able to bind specifically to transthyretin. The receptor can be, for example, an antibody fragment such as an Fab or an $F(ab')_2$ fragment or any other protein or peptide structure being able to specifically bind to transthyretin.

The antibody, antibody fragment or receptor is bound to a solid support such as, e.g., a plastic surface or beads to allow binding and detection of transthyretin. For example, a conventional microtiter plate can be used as a plastic surface. The detection of the binding of transthyretin can be effected, for example, by using a secondary antibody labelled with a detectable group. The detectable group can be, for example, a radioactive isotop or an enzyme like horseradish peroxidase or alkaline phosphatase detectable by adding a suitable substrate to produce, for example, a colour or a fluorescence signal.

The test system can be an immunoassay such as an enzyme-linked immunosorbentassay (ELISA) or an radio immunoassay (RIA). However, any other immunological test system using the specificity of antibodies or fragments of antibodies can be used such as Western blotting or immuno precipitation.

The present invention also provides an array comprising detection molecules for detecting colorectal adenoma and/or colorectal carcinoma in an individual, wherein the detection molecule can be a nucleic acid probe immobilized on a solid support for binding to and detecting of mRNA encoding transthyretin, fragments, mutations, variants or derivatives thereof, or an antibody immobilized on a solid support for binding to and detecting of an epitope of transthyretin, or a receptor immobilized on a solid support for binding to and detecting of an epitope of transthyretin.

The nucleic acid probe can be any natural occurring or synthetic oligonucleotide, as well as cDNA, cRNA and the like.

The described array can be used in a test system according to the invention. The array can be either a micro array or a macro array. The support can be a polymeric material such as nylon or plastic or an inorganic material such as silicon, for example a silicon wafer, or ceramic. Pursuant to a preferred embodiment, glass ($SiO_2$) is used as solid support material. The glass can be a glass slide or glass chip. Pursuant to another embodiment of the invention the glass substrate has an atomically flat surface.

For example, the array can be comprised of immobilized nucleic acid probes able to specifically bind to mRNA of transthyretin being present in a body fluid such as serum. Another preferred embodiment is to produce cDNA by reverse transcription of transthyretin mRNA and to specifically detect the amount of respective cDNA with said array. The array technology is known to the skilled person. A quantification of the measured mRNA or cDNA, respectively, can be effected by comparison of the measured values with a standard or calibration curve of known amounts of transthyretin mRNA or cDNA.

Preferably, different amounts of detection molecules are immobilized each on the solid support to allow an accurate quantification of the level of transthyretin.

Pursuant to another embodiment of the invention, the level of transthyretin is determined by mass spectroscopy.

Using mass spectroscopy the inventors have detected several variants of the transthyretin protein chains having a molecular weight of inter alia 13,776 Da, 13,884 Da or 14,103 Da.

The inventors have found out that especially the level of molecular variants of transthyretin having a molecular weight of 13,776 Da and 13,884 Da is decreased in a body fluid such as serum in case of incidence of colorectal adenoma and/or colorectal carcinoma.

Using mass spectroscopy the inventors have detected several variants of the transthyretin protein chains having a molecular weight of inter alia 13.776 Da, 13.884 Da or 14.103 Da.

The inventors have found out that especially the level of molecular variants of transthyretin having a molecular weight of 13.776 Da and 13.884 Da is decreased in a body fluid such as serum in case of incidence of colorectal adenoma and/or colorectal carcinoma.

Any suitable ionization method in the field of mass spectroscopy known in the art can be employed to ionize the transthyretin molecule, fragments, mutations, variants or derivatives thereof. The ionization methods comprise electron impact (EI), chemical ionization (CI), field ionization (FDI), electrospray ionization (ESI), laser desorption ionization (LDI), matrix assisted laser desorption ionization (MALDI) and surface enhanced laser desorption ionization (SELDI).

Any suitable detection method in field of mass spectroscopy known in the art can be employed to determine the molecular mass of transthyretin, fragments, mutations, variants or derivatives thereof. The detection methods comprise quadrupol mass spectroscopy (QMS), fourier transform mass spectroscopy (FT-MS) and time-of-flight mass spectroscopy (TOF-MS).

Preferably, the mass spectroscopy is a surface enhanced laser desorption ionization-time of flight-mass spectroscopy (SELDI-TOF-MS). Before carrying out a SELDI-TOF-MS, the transthyretin in the isolated sample is preferably immobilized on a chip or solid support with an activated surface. The activated surface comprises preferably immobilized anti-transthyretin antibodies such as, for example, rabbit polyclonal anti-transthyretin antibodies. After binding of the transthyretin to the antibodies, a time-of-flight analysis in a SELDI-TOF mass spectrometer is carried out, which delivers intensity signals for determination of the transthyretin level.

Moreover, mass spectroscopy allows to simultaneously detect other proteins which can have a relevance with respect to the detection of colorectal adenoma and/or colorectal cancer.

In another embodiment of the present invention the sensitivity and/or specificity of the detection of colorectal adenoma and/or colorectal carcinoma is enhanced by detection of another protein in combination with transthyretin.

Another biomarker for colorectal adenoma and/or colorectal carcinoma, the level of which can be determined in addition to the level of transthyretin, comprises a protein or polypeptide having a molecular weight 8,960 Da. The level of said 8,960 Da protein or polypeptide in a sample material has been found to be increased in colorectal adenoma and/or colorectal carcinoma when compared to the level of this protein or polypeptide in samples isolated from healthy individuals.

Therefore, it is preferred to determine the level of said protein having a molecular weight of 8960±9 Da in addition to the level of transthyretin in a body fluid such as serum by mass spectroscopy. The mass spectroscopy is the method of choice to detect and quantify the level of said 8960±9 Da protein.

In another embodiment of the present invention the sensitivity and/or specificity of the detection of colorectal adenoma and/or colorectal carcinoma is enhanced by detection of CEA (carcinoembryonic antigen) and/or CA 19-9 in combination with transthyretin. CEA and CA 19-9 were both analyzed as response indicators and prognostic factors in advanced colorectal carcinoma.

In a further embodiment of the present invention the sensitivity and/or specificity of the detection of colorectal adenoma and/or colorectal carcinoma is enhanced by detection of CA15-3, CA-125 and/or Her-2/neu in combination with transthyretin. CA15-3 is an oncofetal antigen, which is expressed by several carcinomas, and is often measured with other tumor markers. Both CA15-3 and CA-125 are prognostic indicators, mainly for breast cancer, but also in addition to visceral metastases. The amplification of Her-2/neu in breast carcinoma is associated with poor prognosis, short disease-free interval and short survival time. Little is known up to now about the starting point of amplification and the progress of Her-2/neu up to now.

The methods of the present invention can be carried out in combination with other diagnostic methods for detection of colorectal adenoma and/or colorectal carcinoma to increase the overall sensitivity and/or specificity.

Preferably, the methods of the present invention are carried out as an early detection and/or monitoring method. If the results of the methods of the present invention should indicate the incidence of colorectal adenoma and/or colorectal adenoma, further examinations such as colonoscopy or a faecal occult blood testing (FOBT) should be carried out.

The following polyclonal anti-transthyretin antibodies can be used when practicing the invention: PC 066 available from The Binding Site Ltd., Birmingham, England and A 0002, available from DAKO, Hamburg, Germany.

The following figures and example are given for illustrative purposes only. The invention is not to be construed to be limited to the following examples.

EXAMPLE

Unless otherwise stated all methods were carried out following the protocol of the manufacturer of the analytical systems.

Serum Collection and Serum Fractionation

Serum from three groups of human patients were collected and investigated.

Group 1 consisted of 30 patients which were surgical patients treated for non-cancerous diseases such as inguinal hernia, gall bladder stones or diverticulitis. These individuals of group 1 were taken as the group of healthy individuals, i. e. those, who did not suffer from colorectal adenoma and/or colorectal carcinoma.

Group 2 consisted of 29 patients, who were all surgical patients treated for undefined tumors, which turned out to be benign colorectal adenoma.

Group 3 consisted of 28 patients, who were patients having colorectal carcinoma. All these 28 patients suffered from TNM stage III (Tumor, Node, Metastasis stageIII) colorectal carcinoma.

Ethical guidelines and patient confidentiality have been strictly assured and all patients gave written consent to participate in this study. All patients had comparable preoperative preparations such as fasting time and premedication.

Figure 1:
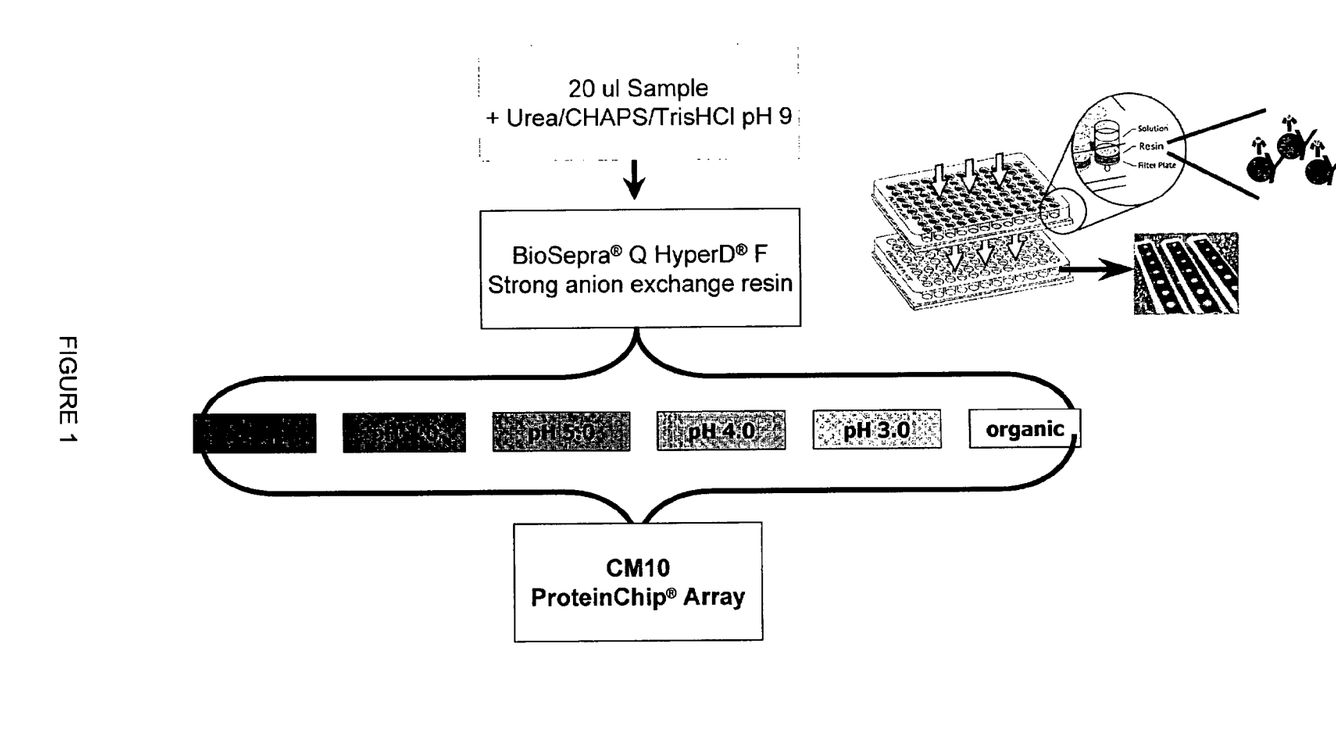
FIG. 1 shows a schematic diagram for fractionating and profiling of serum samples.

Serum from each patient was fractionated by anion exchange chromatography (Serum Fractionation Kit/Q HyperD resin, Ciphergen Biosystems, Inc.) using a 96 well format automation approach (Biomek2000, Ciphergen), according to the protocol of the manufacturer, to reduce some of the interference by the most abundant proteins. As shown in FIG. 1, the fractionation produced 6 fractions containing proteins separated roughly on the basis of the protein pI-value.

From eight patients, all fractions were tested using chromatographic surface ProteinChip® arrays from Ciphergen Biosystems, Inc. The arrays provide relatively high capacity and bind a large variety of proteins and peptides for a wide range of protein profiling and peptide mapping applications. The six serum fractions from eight patients were applied to the following three different protein arrays: SAX-2, a strong anion array with quarternary amine functionality, IMAC, an immobilized metal capture array with a nitriloacetic acid surface and CM10, a weak cation exchange array with carboxylate functionality. Two fractions that gave the highest number of evaluable peaks were selected (fraction 1, fraction 4) for a profiling approach on a chip that showed the lowest data variability (CM10 array). These two fractions were measured in all three groups using Ciphergen ProteinChip® Array CM 10.

Chiphergen ProteinChip® Array Preparation and SELDI-TOF-MS Analysis

CM10 protein arrays were processed in a bioprocessor (Ciphergen Biosystems, Inc.) according to the protocol of manufacturer. Chips were equilibrated with CM10 binding buffer (Ciphergen Biosystems, Inc.) for 2×5 minutes and were subsequently incubated with the serum fractions which had been diluted 1:10 in CM10 binding buffer. After 45 minutes the unbound material was removed and the chips were washed 3 times with CM10 binding buffer and 2 times with water. After drying at room temperature for 10 minutes, 2 applications of 0.05 M sinapinic acid (1.0 µl) were added and the chips were analyzed with the Ciphergen Protein ChipReader (model PBSII).

The Protein ChipReader is a time-of-flight mass spectrometer. The mass values and signal intensities for the detected proteins are transferred to a software, which is supplied by Ciphergen for further in-depth analysis by the ProteinChip Data Analysis Program and Biomarker Wizard Program.

To minimize data variability, measurement was performed within two days using samples from all patient groups randomly distributed on the chips. As a standard control for normalization, pooled normal serum was used parallel to all measurements.

The mass spectra of proteins were generated by using an average of 195 laser shots at a laser intensity of 185. The detector was run at a sensitivity of 7. For data acquisition, the detection size range was set between 2,000 and 40,000 Da.

The laser was focused at 10,000 Da. The data were analyzed with the ProteinChip Data Analysis Program (version 3.1, Ciphergen Biosystems) and with the Biomarker Wizard Program (version 3.1, Ciphergen Biosystems). The peak intensities were normalized to the total ion current.

Results

In this experiment, differentially expressed proteins between serum from non-carcinoma patients (Group 1) and serum from patients with colorectal adenoma (Group 2) and colorectal carcinoma (Group 3) were identified. As shown in Table 1, six peaks could be identified in fraction 1 that showed the mean-values of intensity of highly significant differences ($p \leq 0.0000001$) between healthy patients (non-cancer patients), colorectal adenoma patients and colorectal carcinoma patients. As shown in Table 2, fraction 4 provided an additional set of potential biomarkers that differed significantly between the three groups ($p \leq 0.0000001$).

TABLE 1

Biomarkers selected after processing of fraction 1 of each serum sample on Ciphergen chips. The p-values were generated with nonparametric tests from the Biomarker Wizzard application. N gives the transthyretin level for 'healthy' patients, A for colorectal adenoma patients and Ca for colorectal carcinoma patients. StDev is the standard deviation of the measurement.

| M/Z | P-Value | Mean N | StDev N | Mean A | StDev A | Mean Ca | StDev Ca |
| --- | --- | --- | --- | --- | --- | --- | --- |
| 5820 | 0.0000000 | 1.320 | 0.633 | 1.800 | 1.205 | 2.811 | 1.374 |
| 6121 | 0.0000000 | 5.074 | 1.895 | 5.884 | 1.936 | 8.116 | 3.237 |
| 6139 | 0.0000001 | 3.381 | 1.359 | 4.013 | 1.440 | 5.346 | 2.346 |
| 5916 | 0.0000002 | 41.119 | 13.267 | 47.122 | 14.205 | 58.580 | 14.654 |
| 8632 | 0.0000003 | 1.043 | 0.710 | 1.688 | 1.194 | 2.079 | 1.386 |
| 5931 | 0.0000004 | 20.077 | 8.925 | 23.771 | 8.881 | 30.289 | 12.146 |

TABLE 2

Biomarkers selected after processing of fraction 4 of each serum sample on Ciphergen chips. The p-values were generated with nonparametric tests from the Biomarker Wizzard application. N gives the transthyretin level for 'healthy' patients, A for colorectal adenoma patients and Ca for colorectal carcinoma patients. StDev is the standard deviation of the measurement.

| M/Z | P-Value | Mean N | StDev N | Mean A | StDev A | Mean Ca | StDev Ca |
|---|---|---|---|---|---|---|---|
| 6850 | ≦0.0000001 | 1.10 | 0.29 | 0.69 | 0.21 | 0.81 | 0.33 |
| 6885 | ≦0.0000001 | 1.16 | 0.30 | 0.79 | 0.25 | 0.74 | 0.31 |
| 7055 | ≦0.0000001 | 0.75 | 0.16 | 0.55 | 0.15 | 0.51 | 0.20 |
| 13770 | ≦0.0000001 | 1.73 | 0.46 | 1.16 | 0.33 | 1.01 | 0.49 |
| 13900 | ≦0.0000001 | 3.66 | 0.88 | 2.59 | 0.81 | 2.30 | 1.04 |
| 14160 | ≦0.0000001 | 1.93 | 0.44 | 1.47 | 0.41 | 1.27 | 0.48 |
| 4975 | ≦0.0000001 | 0.31 | 0.15 | 0.49 | 0.26 | 0.72 | 0.45 |
| 6645 | ≦0.0000001 | 9.41 | 2.44 | 6.05 | 2.03 | 6.86 | 3.19 |
| 14060 | ≦0.0000001 | 3.40 | 0.83 | 2.56 | 0.81 | 2.23 | 0.89 |
| 6950 | ≦0.0000001 | 2.45 | 0.74 | 1.79 | 0.75 | 1.69 | 0.79 |
| 51485 | ≦0.0000001 | 0.15 | 0.03 | 0.14 | 0.02 | 0.18 | 0.04 |
| 22330 | ≦0.0000001 | 0.37 | 0.04 | 0.42 | 0.05 | 3.49 | 0.43 |
| 5765 | ≦0.0000001 | 0.86 | 0.22 | 1.00 | 0.37 | 1.35 | 0.45 |
| 28100 | ≦0.0000001 | 2.82 | 0.76 | 2.11 | 0.70 | 1.79 | 0.73 |
| 5915 | ≦0.0000001 | 0.59 | 0.18 | 0.61 | 0.14 | 0.88 | 0.33 |
| 17415 | ≦0.0000001 | 0.83 | 0.30 | 0.62 | 0.25 | 0.52 | 0.22 |

Several proteins were tested as single biomarkers and in combination with other markers using the Biomarker Pattern Software. One protein with a molecular weight of 13,770 Da (p 13,770) was found to discriminate between adenoma/carcinoma patients and healthy controls giving a sensitivity of 75% and a specificity of 90%.

Figure 2:
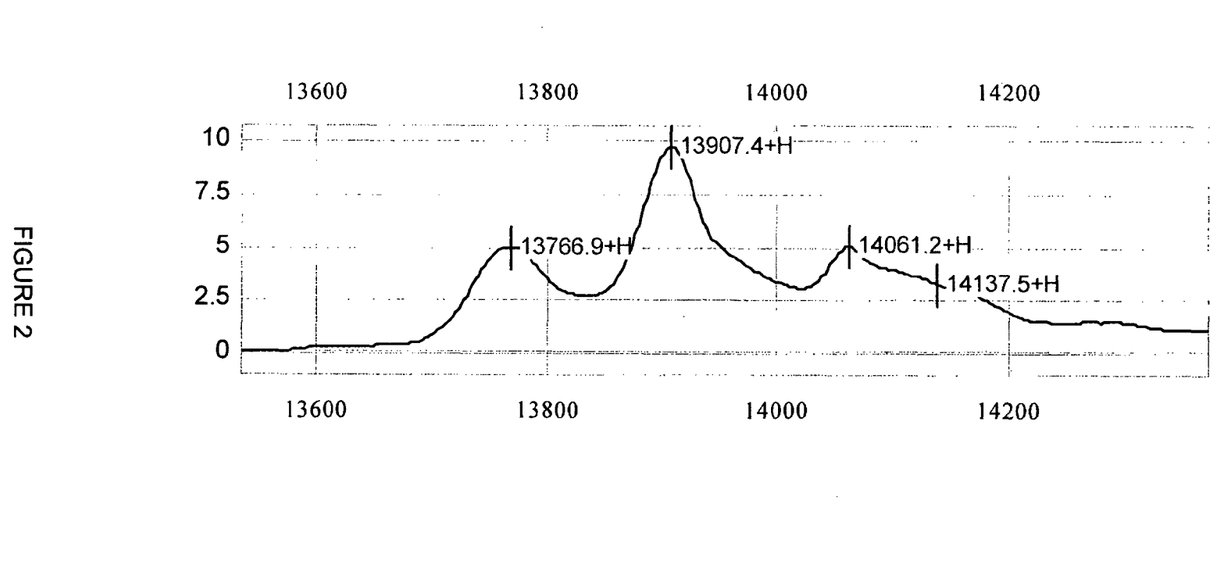
FIG. 2 shows a SELDI-TOF profile.
Figure 3:
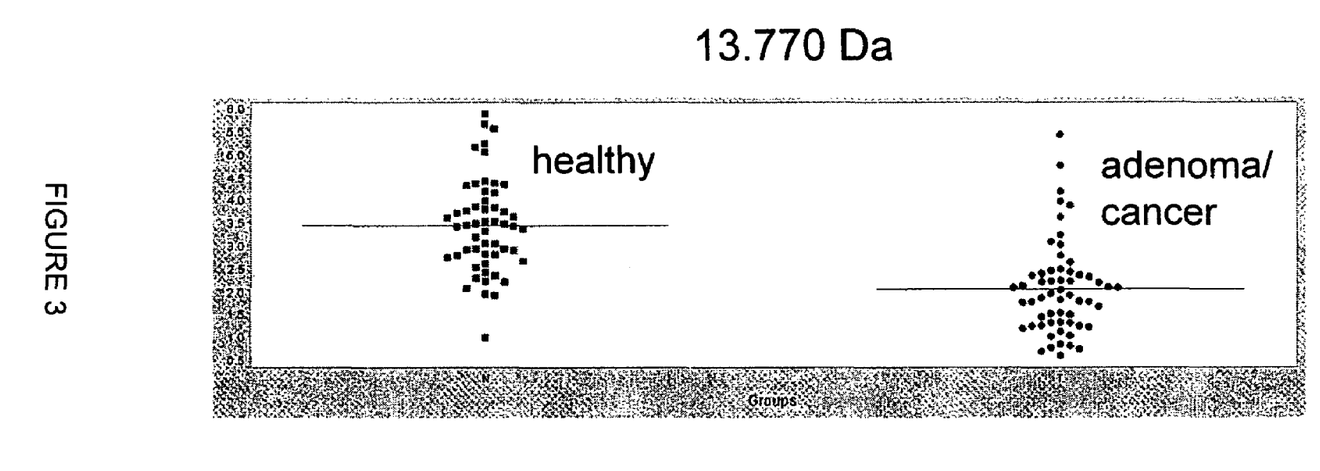
FIG. 3 shows a differention of healthy individuals from adenoma/carcinoma individuals.

FIG. 2 shows a SELDI profile demonstrating the biomarker. FIG. 3 shows the discrimination of healthy patients from adenoma/carcinoma patients in a scatter plot. The intensities of the biomarker having a molecular weight of 13770 Da (p 13,370) are significantly lower in the serum of adenoma/cancer patients than in healthy patients.

Figure 4:
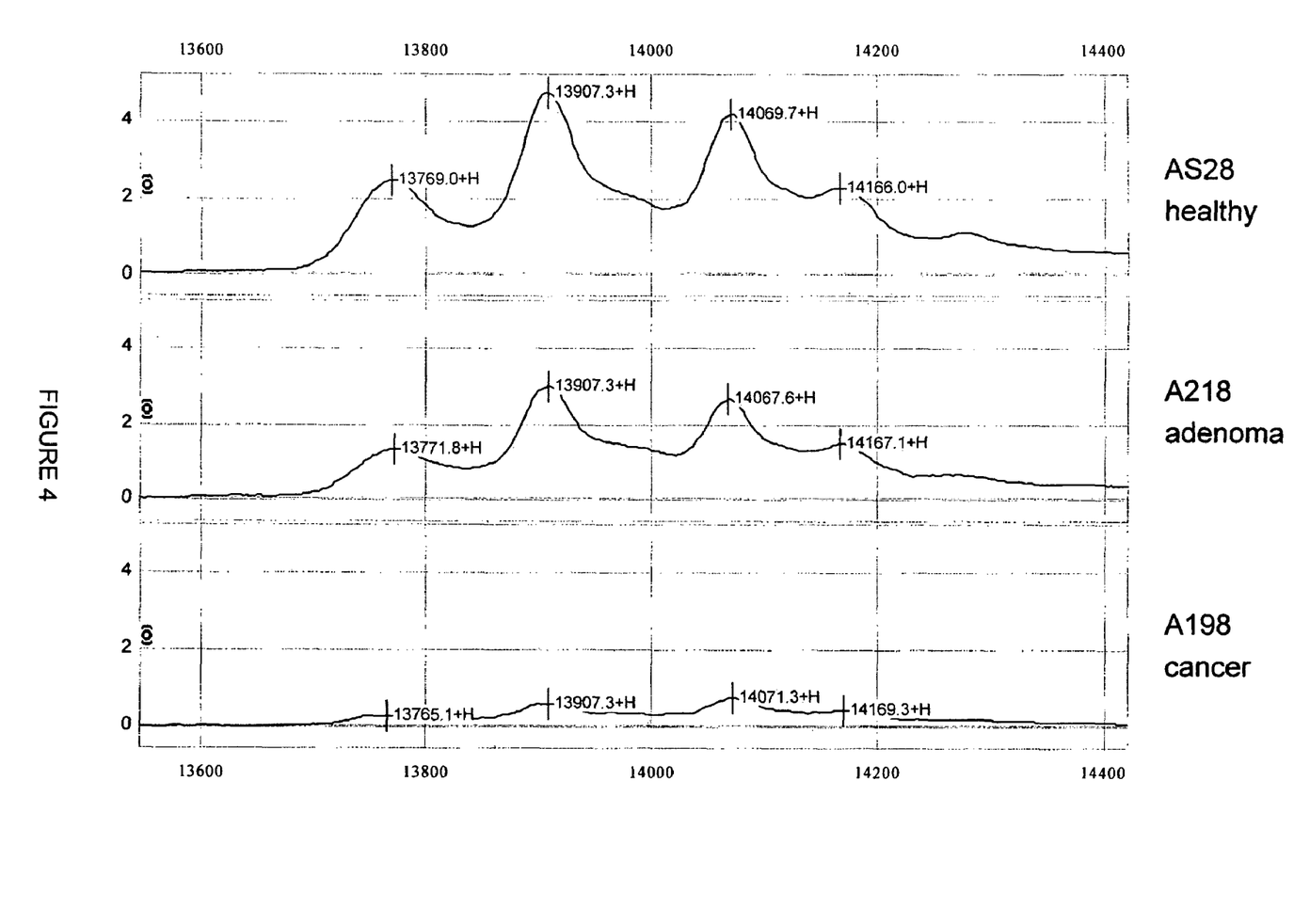
FIG. 4 shows SELDI-TOF protein profiles of serum fractions from three different individuals

FIG. 4 shows SELDI-TOF protein profiles of serum fraction no. 4 from healthy, adenoma patients and cancer patients. As can be seen the intensity of the p 13,370 peak decreases significantly from healthy patients over colorectal adenoma patients to colorectal cancer patients.

In combination with a second marker protein (MW 8,960 Da, fraction no. 1), separation of healthy patients from adenoma/carcinoma patients was significantly improved. 30 non-adenoma/carcinoma (healthy) patients, 20 of 29 colorectal adenoma patients as well as 20 of 28 colorectal carcinoma patients were correctly separated. With this combination, a sensitivity of 70% and a specificity of 100% were achieved.

Identification of Transthyretin

Using immunoaffinity capture and immunoprecipitation tests, the 13,770 Da protein was identified as transthyretin. Protein Chip Immunoaffinity Capture of Transthyretin The immunoaffinity capture was performed using a Protein G Array (Ciphergen Biosystems, Inc.) following the manufacturer's protocol. A rabbit polyclonal anti-transthyretin antibody A0002 (Dako, Hamburg, Germany), diluted to a concentration of 0.2 µg/µl in PBS. 2 µl per spot were pipetted on the array and subsequently incubated for 24 h at 4° C. in a humidified chamber. Unbound antibody was removed by washing with washing buffer (0.5% (v/v)) triton X-100 in PBS. After drying, the array was inserted into a bioprocessor (Ciphergen Biosystems, Inc.) for sample incubation. 2 µA of serum fractions containing high and low amounts of 13,770 Da protein (colorectal adenoma/carcinoma patients versus healthy patients) were added to the chip and incubated for 1 h at room temperature on a horizontal shaker. After washing with PBS and HEPES buffer the array was air dried for 10 minutes and 0.6 µl saturated sinapinic acid matrix was added to each spot. The array was measured using the following parameters: the laser intensity was set to 185, the sensitivity to 7. The detection size range was set to between 200 and 200, 000 Da, the laser was focused at 10,000 Da.

After binding to the antibody coated array, four protein peaks of different molecular weight (approximately 13,761 Da, 13,914 Da, 14,102 Da and 14,292 Da) have been identified, suggesting that transthyretin occurs in different molecular variants.

Figure 5:
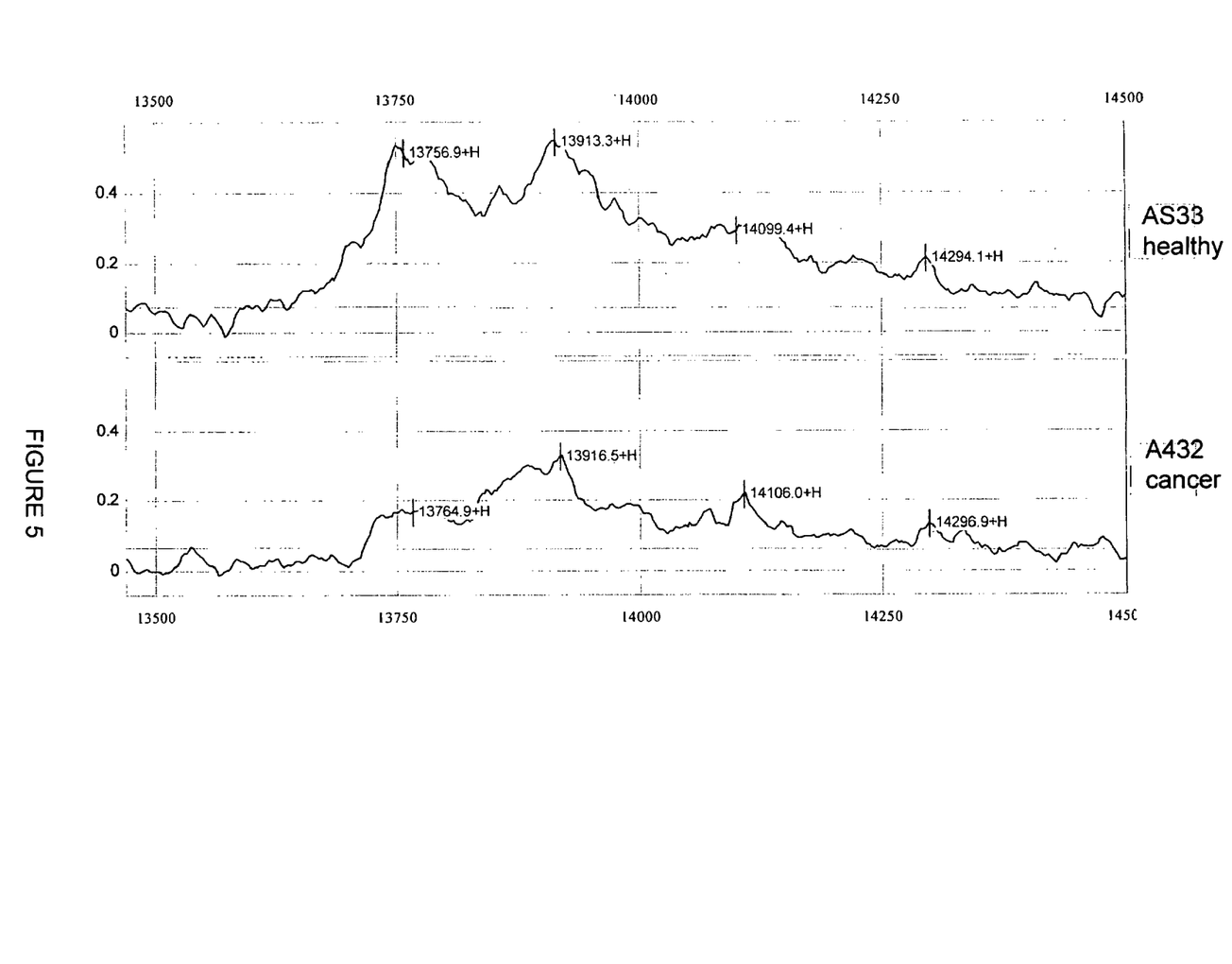
FIG. 5 shows SELDI immunoaffinity capture of transthyretin and its potential derivatives.

FIG. 5 shows a comparison of the signal intensities between a healthy patient and a carcinoma patient.

Figure 6:
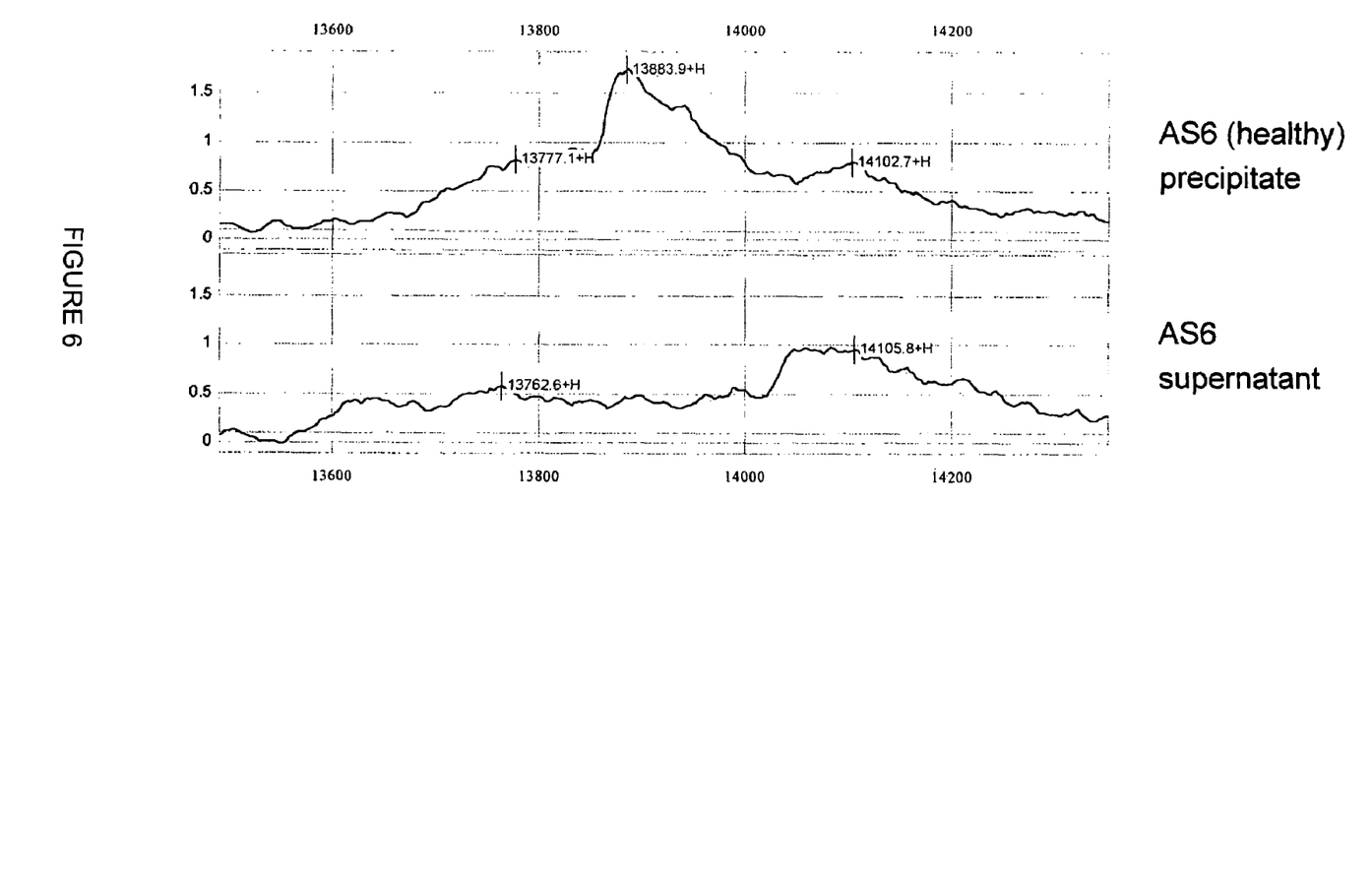
FIG. 6 shows immunoprecipitation with an anti-transthyretin antibody.

Finally, an immunoprecipitation was carried out. 50 µl of serum of fraction 4 from different patients were incubated with 15 µl (6.75 µg) of the polyclonal antibody against transthyretin for 2 hours at 4° C. A negative control was performed in the same way without antibody. 50 µl of protein A/G agarose (Pierce, Rockford, Ill.) was added and incubated at 4° C. over night. After centrifugation at 3300 xg, the supernatants were removed and stored separately. The pellet was resuspended in 20 µl buffer (9M urea, 2% Chaps, 50 mM Tris-HC1, pH9) to detach the proteins from the protein A/G-agarose. Precipitate as well as supernatant were diluted 1:10 in CM 10 binding buffer. Three proteins with different molecular weights (13,776 Da, 13,884 Da, 14,103 Da) were immunoprecipitated with an anti-transthyretin antibody. From FIG. 6 it can be seen that in the supernatant, the amount of two variants (13,776 Da and 13,884 Da) was significantly reduced, whereas the amount of the variant with the highest molecular weight (14,103 Da) remained unchanged.

This shows that the transthyretin protein chains having a molecular weight of about 13,776 Da and about 13,884 Da are important biomarkers for the detection of colorectal adenoma and/or colorectal carcinoma.

The invention claimed is:
1. A method for detecting colorectal adenoma comprising:
 a) providing an isolated sample which has been taken from an individual,
 b) determining the level of transthyretin protein in said isolated sample,
 c) comparing the determined level of transthyretin with a reference value, wherein said reference value is a level of transthyretin protein present in at least one sample taken from at least one healthy individual, and d) determining the presence of colorectal adenoma when the level of transthyretin in said sample is lower than said reference value and higher compared to a sample taken from a colorectal carcinoma patient.

2. A method of determining the presence of colorectal adenoma during the course of treatment of colorectal adenoma comprising:

a) providing an isolated sample which has been taken from an individual, b) determining the level of transthyretin protein in said isolated sample, and c) comparing the determined level of transthyretin with a reference value, wherein said reference value is a level of transthyretin protein present in at least one sample taken from at least one healthy individual, and d) determining the presence of colorectal adenoma when the level of transthyretin in said sample is lower than said reference value and higher compared to a sample taken from a colorectal carcinoma patient.

3. The method of claim 1, wherein the reference value is calculated as the average level of transthyretin determined in a plurality of isolated samples from healthy individuals.

4. The method of claim 1, wherein the reference value is an individual reference value calculated as the average level of transthyretin determined in a plurality of isolated samples taken from said individual over a period of time.

5. The method of claim 1, wherein the transthyretin is modified by cysteinylation and/or glutationylation.

6. The method of claim 1, wherein the isolated sample material is a body fluid.

7. The method of claim 6, wherein the body fluid is selected from the group consisting of blood, blood plasma, serum, bone marrow, stool, synovial fluid, lymphatic fluid, cerebro spinal fluid, sputum, urine, mother's milk, sperm, exudates and mixtures thereof.

8. The method of claim 1, wherein said method further comprises determining the level of carcinoembryonic antigen (CEA) in said sample and wherein the level of said carcinoembryonic antigen (CEA) in said sample is elevated if colorectal adenoma is present.

9. The method of claim 1, wherein the level of transthyretin in said sample is determined by an immunoassay.

10. The method of claim 1, wherein the method is carried out in combination with other diagnostic methods for colorectal adenoma.

11. The method of claim 2, wherein the reference value is calculated as the average level of transthyretin determined in a plurality of isolated samples from healthy individuals.

12. The method of claim 2, wherein the reference value is an individual reference value calculated as the average level of transthyretin determined in a plurality of isolated samples taken from said individual over a period of time.

13. The method of claim 2, wherein the transthyretin is modified by cysteinylation and/or glutationylation.

14. The method of claim 2, wherein the isolated sample material is a body fluid.

15. The method of claim 14, wherein the body fluid is selected from the group consisting of blood, blood plasma, serum, bone marrow, stool, synovial fluid, lymphatic fluid, cerebro spinal fluid, sputum, urine, mother's milk, sperm, exudates and mixtures thereof.

16. The method of claim 2, wherein said method further comprises determining the level of carcinoembryonic antigen (CEA) in said sample and wherein the level of said carcinoembryonic antigen (CEA) in said sample is elevated if colorectal adenoma is present.

17. The method of claim 2, wherein the level of transthyretin in said sample is determined by an immunoassay.

18. The method of claim 2, wherein the method is carried out in combination with other diagnostic methods for colorectal adenoma.

19. The method of claim 1, wherein the level of transthyretin in said sample is determined by mass spectroscopy.

20. The method of claim 2, wherein the level of transthyretin in said sample is determined by mass spectroscopy.

21. The method of claim 1, wherein said method further comprises determining the level of CA 19-9 in said sample and wherein the level of said CA 19-9 in said sample is elevated if colorectal adenoma is present.

22. The method of claim 2, wherein said method further comprises determining the level of CA 19-9 in said sample and wherein the level of said CA 19-9 in said sample is elevated if colorectal adenoma is present.

* * * * *